(12) United States Patent
Ko et al.

(10) Patent No.: US 9,116,077 B2
(45) Date of Patent: Aug. 25, 2015

(54) METHOD AND SYSTEM FOR ESTIMATING FOOD COMMODITY INTAKE

(75) Inventors: Sang Hoon Ko, Seoul (KR); Seung Won Kim, Gyeonggi-Do (KR); Ki Sung Kwon, Chungcheongnam-do (KR); Jae Ho Oh, Chungcheongbuk-Do (KR); Jung Ah Do, Chungcheongbuk-do (KR); Joong Keun Lee, Seoul (KR); Hee Dong Woo, Chungcheongbuk-do (KR)

(73) Assignees: Sejong University Industry Academy Cooperation Foundation, Seoul (KR); Ministry of Food and Drug Safety, Seoul (KR)

( * ) Notice: Subject to any disclaimer, the term of this patent is extended or adjusted under 35 U.S.C. 154(b) by 272 days.

(21) Appl. No.: 13/581,987

(22) PCT Filed: Jun. 27, 2011

(86) PCT No.: PCT/KR2011/004644
§ 371 (c)(1),
(2), (4) Date: Dec. 7, 2012

(65) Prior Publication Data
US 2013/0186695 A1 Jul. 25, 2013

(51) Int. Cl.
*G06F 19/00* (2011.01)
*G06F 17/30* (2006.01)
(Continued)

(52) U.S. Cl.
CPC .............. *G01N 5/00* (2013.01); *G01G 19/4146* (2013.01); *G06F 19/3475* (2013.01); *G06F 19/3481* (2013.01); *G06Q 10/00* (2013.01); *G09B 19/0092* (2013.01)

(58) Field of Classification Search
CPC ............ G01G 19/4146; G06F 19/3475; G06F 19/3481; G09B 19/0092; G06Q 10/00; G01N 5/00
See application file for complete search history.

(56) References Cited

U.S. PATENT DOCUMENTS 4,575,804 A * 3/1986 Ratcliff .......................... 708/133
4,807,169 A * 2/1989 Overbeck ...................... 708/200
(Continued)

FOREIGN PATENT DOCUMENTS

WO WO 2013/002427 A1 * 1/2013 ............... G01N 5/00

*Primary Examiner* — Randy W Gibson
(74) *Attorney, Agent, or Firm* — Mintz Levin Cohn Ferris Glovsky and Popeo, P.C.; Kongsik Kim

(57) ABSTRACT

Disclosed are a method and a system for estimating food commodity intakes. The method includes (a) obtaining a food intake of a food searched as a subject to be estimated for food commodity intake based on food intake database, (b) obtaining a material mix ratio of the food searched based on the material mix ratio database and estimating a material mix ratio intake using the food intake, (c) detecting whether or not the material contained in the material mix ratio intake estimation results is a food commodity, (d) accumulating a weight data of the material that is detected to be a food commodity among the materials obtained from the material mix ratio intake estimation results, (e) repeatedly performing operations (b) to (d) on materials that are not food commodities, until all of the materials contained in the material mix ratio intake estimation results become food commodities, and (f) summing the accumulated weight data of each food commodity to estimate a food commodity intake of the food, when all of the materials contained in the material mix ratio intake estimation results are food commodities. According to the present invention, more accurate food intake data can be conveniently estimated by converting all ingredients of mixed foods into food commodities.

8 Claims, 2 Drawing Sheets

(51) Int. Cl.
*G01N 5/00* (2006.01)
*G01G 19/414* (2006.01)
*G09B 19/00* (2006.01)
*G06Q 10/00* (2012.01)

(56) References Cited

U.S. PATENT DOCUMENTS

| | | | | |
|---|---|---|---|---|
| 4,911,256 | A | * | 3/1990 | Attikiouzel ............... 177/25.16 |
| 5,033,561 | A | * | 7/1991 | Hettinger .................. 177/25.16 |
| 5,388,043 | A | * | 2/1995 | Hettinger .................... 600/300 |
| 5,841,115 | A | * | 11/1998 | Shepley ........................ 235/375 |
| 5,960,440 | A | * | 9/1999 | Brenner et al. ..................... 1/1 |
| 6,024,281 | A | * | 2/2000 | Shepley ........................ 235/375 |
| 6,859,215 | B1 | * | 2/2005 | Brown et al. ................. 715/811 |
| 6,978,221 | B1 | * | 12/2005 | Rudy ............................ 702/173 |
| 2003/0076983 | A1 | * | 4/2003 | Cox .............................. 382/110 |
| 2004/0118618 | A1 | * | 6/2004 | Davidson et al. .......... 177/25.13 |
| 2005/0184148 | A1 | * | 8/2005 | Perlman ........................ 235/383 |
| 2007/0050058 | A1 | * | 3/2007 | Zuziak et al. ................... 700/90 |
| 2008/0091705 | A1 | * | 4/2008 | McBride et al. ............. 707/102 |
| 2010/0038149 | A1 | * | 2/2010 | Corel ........................ 177/25.16 |
| 2010/0332571 | A1 | * | 12/2010 | Healey et al. ................ 707/912 |
| 2011/0168456 | A1 | * | 7/2011 | Sharawi et al. ............ 177/25.16 |
| 2013/0025944 | A1 | * | 1/2013 | Batsikouras ................ 177/25.13 |
| 2013/0029298 | A1 | * | 1/2013 | Batsikouras .................. 434/127 |
| 2013/0157232 | A1 | * | 6/2013 | Ehrenkranz .................. 434/127 |
| 2013/0186695 | A1 | * | 7/2013 | Ko et al. ........................... 177/1 |

* cited by examiner

METHOD AND SYSTEM FOR ESTIMATING FOOD COMMODITY INTAKE

CROSS-REFERENCES TO RELATED APPLICATIONS

This application is a U.S. national phase application, pursuant to 35 U.S.C. §371, of PCT/KR2011/004644, filed Jun. 27, 2011, designating the United States. The entire contents of the aforementioned patent applications are incorporated herein by this reference.

BACKGROUND OF THE INVENTION

1. Field of the Invention

The present invention relates to a method and a system for estimating food commodity intakes. More specifically, the present invention relates to a method and a system for estimating food commodity intakes capable of more accurately estimating food intake data by converting all ingredients of mixed foods into food commodities.

2. Description of the Related Art

It is necessary to obtain the amount of pesticides remaining in foods, and objective and reasonable information associated with food intakes affected by individual difference, in order to evaluate exposure of harmful substances including chemical substances such as pesticides and contaminants such as heavy metals that remain in foods. In domestic, databases and information on residual pesticides, and the type and amount of heavy metals and the like, of respective crops through monitoring of harmful substances for several years are obtained, but information on intake of respective crops and cooked and processed foods using the same is unsatisfactory.

A variety of programs used for obtaining the intake of foods, an acceptable daily intake, food intakes of nutrient components and the like can be calculated based on nutrition survey databases of respective nations. However, a common problem of these programs is that, since although raw materials can be seen through the recipe of one food, but other processed foods may be contained in these raw materials, the intake of food commodities cannot be accurately analyzed.

For example, bibimbap is a mixed food prepared from raw materials such as rice, red pepper paste (gochujang), lettuce and carrot. Among these materials, lettuce and carrot are food commodities, but red pepper paste is a mixed food containing different food commodities. Food commodity means a minimum-unit element constituting a food. It is possible to reasonably and objectively calculation of the amount of substances remaining in foods and evaluation of the risk thereof, when information on consumers and intake of food commodities can be objectively obtained. National nutrition survey food intake databases provide information associated with the aforementioned food commodities such as lettuce, carrot, red pepper paste as well as information associated with the mixed food. For this reason, there is a need to study a method for estimating food commodity intakes from this information.

SUMMARY OF THE INVENTION

Therefore, the present invention has been made in view of the above problems, and it is one object of the present invention to provide a method and a system for estimating a food commodity intake capable of more accurately estimating food intake databases by converting all ingredients of a mixed food into food commodities.

In accordance with one aspect of the present invention, provided is a method for estimating a food commodity intake including: (a) obtaining a food intake of a food searched as a subject to be estimated for food commodity intake based on food intake database; (b) obtaining a material mix ratio of the food searched based on the material mix ratio database and estimating a material mix ratio intake using the food intake; (c) detecting whether or not the material contained in the material mix ratio intake estimation results is a food commodity; (d) accumulating a weight data of the material that is detected to be a food commodity among the materials obtained from the material mix ratio intake estimation results; (e) repeatedly performing operations (b) to (d) on materials that are not food commodities, until all of the materials contained in the material mix ratio intake estimation results become food commodities; and (f) summing the accumulated weight data of each food commodity to estimate a food commodity intake of the food, when all of the materials contained in the material mix ratio intake estimation results are food commodities.

The method may further include: updating the estimated food commodity intake on food commodity intake databases.

The method may further include: adding a material contained in the intake database, among materials contained in the food the material mix ratio intake estimation results, to an unregistered commodity database.

The food intake database may be established from the results obtained from the Korea National Health And Nutrition Examination Survey (KNHANES).

In accordance with another aspect of the present invention, provided is a computer-readable storage medium storing a program to execute the method.

In accordance with yet another aspect of the present invention, provided is a system for estimating a food commodity intake including: a material mix ratio intake conversion portion to estimate a material mix ratio intake of a material mix ratio of a food searched using a food intake and a material mix ratio database of the food searched as a subject to be estimated for a food commodity intake based on the food intake database; a food commodity detection portion to detect whether or not the material contained in the material mix ratio intake estimation results is a food commodity; a food commodity data accumulation portion to accumulate a weight data of the material that is detected to be a food commodity contained in the material mix ratio intake estimation results; and a food commodity intake conversion portion to calculate a total of the accumulated weight data of each food commodity to estimate a food commodity intake of the food, when all of the materials contained in the material mix ratio intake estimation results are food commodities, wherein the system repeats conversion of material mix ratio intake, detection of food commodity and accumulation of material weight data on the materials that are not food commodities, until all of the materials contained in the material mix ratio intake become food commodities.

The food commodity intake conversion portion may update the estimated food commodity intake on the food commodity intake database.

The food intake database may be established from the results obtained from the Korea National Health And Nutrition Examination Survey (KNHANES).

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION OF THE INVENTION

First of all, technical terms used herein will be defined prior to the description of embodiments of the present invention.

A food commodity is a raw material-concentrated product such as agricultural product, marine product, or livestock product and is used as a basic unit for determining the standards and specifications of chemical residues and realizing safety management. The food commodity is composed of a single food commodity or a mixture of food commodities and materials. The mixed food contains a food commodity and materials. A food mentioned below may include a mixed food and a food commodity.

Next, embodiments of the present invention will be described with reference to the annexed drawings in more detail to an extent that the embodiments can be easily accomplished by a person having common knowledge in the art pertaining to the present invention.

Figure 1:
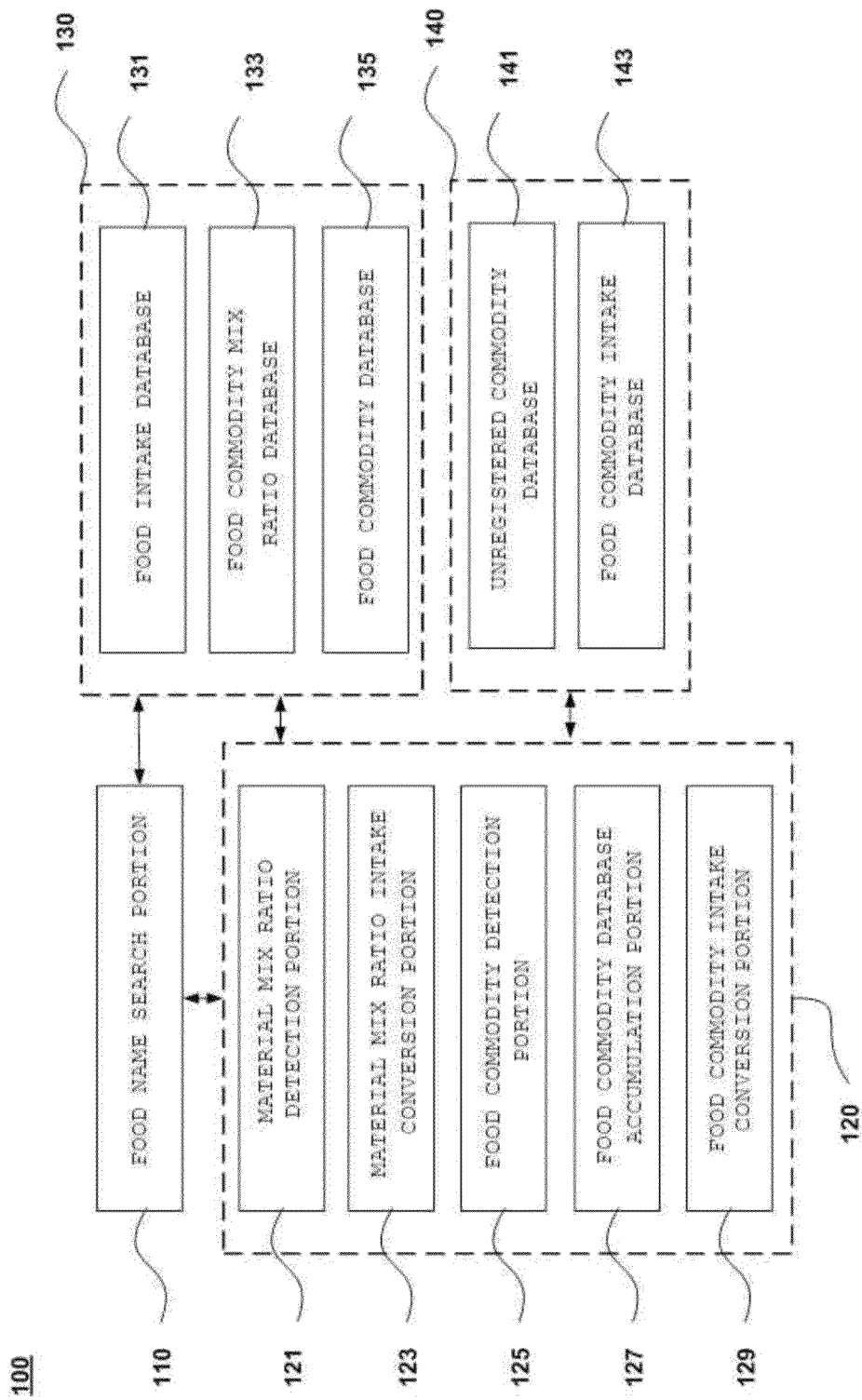
FIG. 1 is a block diagram illustrating a system for estimating food commodity intake according to one embodiment of the present invention.

FIG. 1 is a block diagram illustrating a system for estimating a food commodity intake according to one embodiment of the present invention.

Referring to FIG. 1, the system for estimating food commodity intake 100 includes a food name search portion 110, an algorithm portion 120, an outer database portion 130 and an inner database portion 140. The algorithm portion 120 may include a material mix ratio detection portion 121, a material mix ratio intake conversion portion 123, a food commodity detection portion 125, a food commodity database accumulation portion 127 and a food commodity intake conversion portion 129.

The outer database portion 130 includes a food intake database 131, a food commodity mix ratio database 133 and a food commodity database 135, and the inner database portion 140 includes an unregistered commodity database 141 and a food commodity intake database 143.

The food name search portion 110 helps a user to conveniently search a specific food based on food names shown in the National Nutrition Survey Table.

For example, when a user searches an orange juice, orange juices of a great number of brands are displayed and one is selected therefrom. For example, the selection is carried out such that the orange juice products are classified into orange juice products supplemented with sugar and pure orange juice products. As a result, the user can conveniently and accurately select the food, the subject for estimating food commodity intake.

The outer database portion 130 provides various databases required for estimating food commodity intake according to the present invention in response to the request of the algorithm portion 120 and, specifically, the food intake database 131 can be established based on the results obtained from the Korea National Health And Nutrition Examination Survey (KNHANES) and includes information on daily intake in a year (hereinafter, referred to as "food intake") of respective foods. In some embodiments, databases using national nutrition surveys as well as other intake evaluation may be used. For example, food intake databases established in respective nations may be used. In this case, food commodity intakes obtained according to the present invention may be determined while taking into consideration conditions and situations of respective nations.

The food commodity mix ratio database 133 includes information on material mix ratios of foods. For example, in a case of a hamburger, the food commodity mix ratio database 133 includes information shown in Table 1.

TABLE 1

| Hamburger commodity mix ratio | |
|---|---|
| Material | Ratio |
| Hamburger bread | 0.09375 |
| Cheese (slice) | 0.046875 |
| Mushroom | 0.078125 |
| Lettuce | 0.15625 |
| Pickles | 0.15625 |
| Tomato | 0.15625 |
| Onion | 0.078125 |
| Beef | 0.078125 |
| Pork | 0.09375 |
| Ketchup | 0.03125 |
| Mayonnaise | 0.03125 |
| Total | 1 |

The food commodity database 135 stores information on food commodity and supplies the information to a food commodity detection portion 125 so that the food commodity detection portion 125 detects whether the material contained in the estimated material mix ratio intake results is a food commodity.

The inner database portion 140 stores various data produced during the food commodity intake estimation process. Specifically, the unregistered commodity database 141 may be established with information on materials not registered in the KNHANES material list. Furthermore, when materials not shown in the food commodity mix ratio of Table 1 are present during the food commodity intake estimation process, the materials are registered in the unregistered commodity database 141 and an operator then estimates food intakes or food commodity mix ratios of the corresponding unregistered material and reflects the estimated values to the food intake database 131 and the food commodity mix ratio database 133.

The food commodity intake database 143 establishes the food commodity intake estimation results according to the present invention as a database.

The algorithm portion 120 performs data processing to estimate food commodity intakes according to the present invention and a detailed explanation thereof will be given below.

The material mix ratio decision portion 121 determines whether the material mix ratio of food searched by the user through the food name search portion 110 based on the food commodity mix ratio database 133 is present or not.

The material mix ratio intake conversion portion 123 estimates material mix ratio intakes, which are expressed based on weights of respective materials constituting the corresponding food using the corresponding food weight (food intake) and material mix ratio information.

The food commodity detection portion 125 detects whether the material contained in the material mix ratio intake is a food commodity.

The food commodity database accumulation portion 127 accumulates weight data of material which is detected to be a food commodity by the food commodity detection portion 125.

The food commodity intake conversion portion 129 sums all of the finally accumulated weight data of each food commodity of the searched food and updates the data on the food commodity intake database 143.

Figure 2:
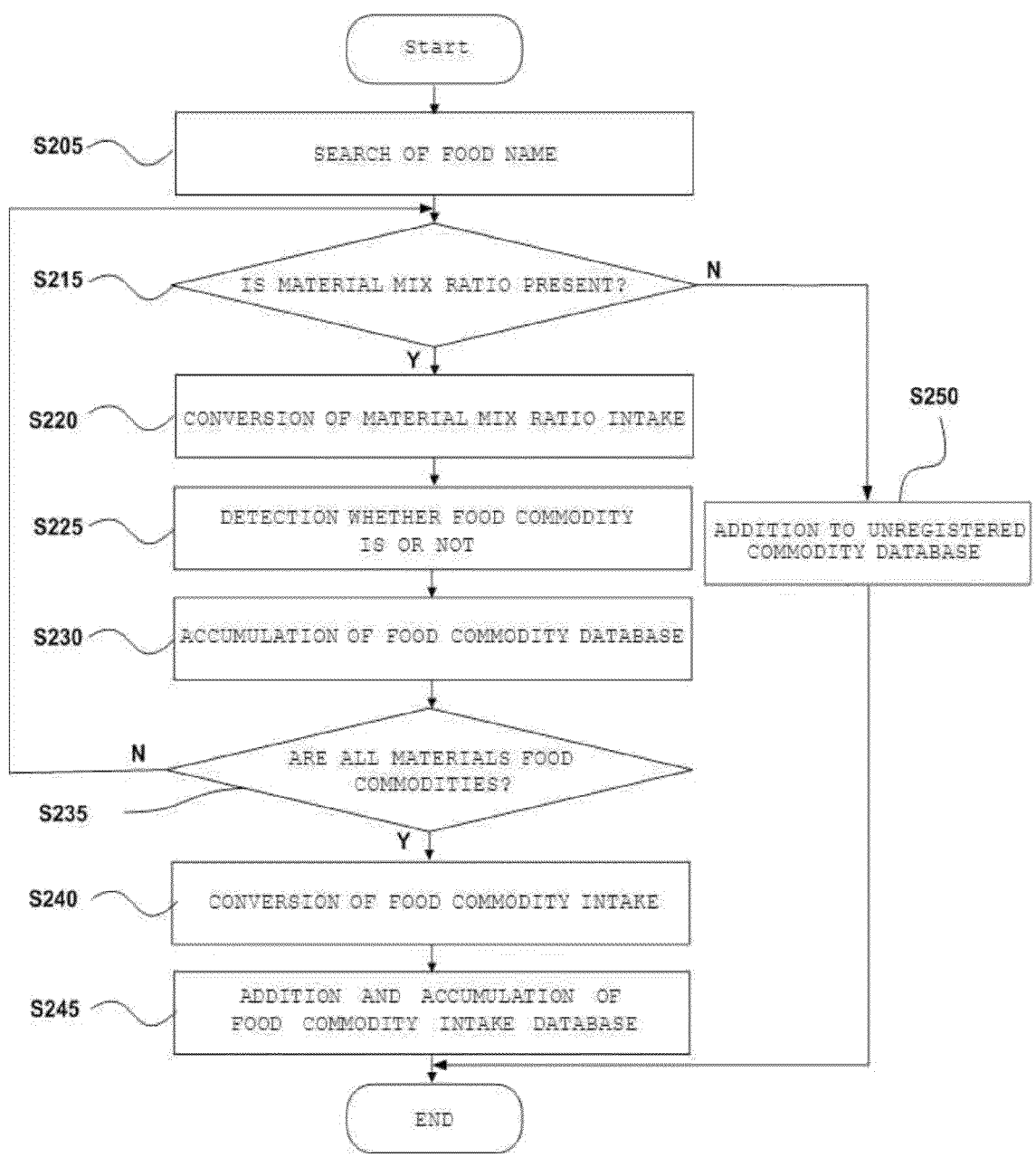
FIG. 2 is a flow diagram illustrating a system for estimating food commodity intake according to the present invention.

Referring to FIG. 2, an operation method of the system for estimating a food commodity intake according to the present invention will be described in detail.

FIG. 2 is a flow chart illustrating a method for estimating food commodity intake according to the present invention.

Referring to FIG. 2, first, the food name search portion 110 helps a user to conveniently search a specific food that the user wants to confirm a food commodity intake, based on food names shown in the national nutrition survey table (S205).

Next, the material mix ratio decision portion 121 detects whether a material mix ratio of the food searched using the food commodity mix ratio database 133 is present or not (S215).

When the material mix ratio is present (S215—Y), the material mix ratio intake conversion portion 123 estimates a material mix ratio intake, which is expressed based on a weight of each material constituting the food searched as shown in the following Table 2, using food weight (food intake) and material mix ratio information (S220).

Table 2 shows an estimated material mix ratio intake of hamburger. Hereinafter, an example in which the food searched for food commodity intake estimation is a hamburger will be described.

TABLE 2

Hamburger

| Material | Unit (g) | Ratio |
|---|---|---|
| Hamburger bread | 60 | 0.09375 |
| Cheese (slice) | 30 | 0.046875 |
| Mushroom | 50 | 0.078125 |
| Lettuce | 100 | 0.15625 |
| Pickles | 100 | 0.15625 |
| Tomato | 100 | 0.15625 |
| Onion | 50 | 0.078125 |
| Beef | 50 | 0.078125 |
| Pork | 60 | 0.09375 |
| Ketchup | 20 | 0.03125 |
| Mayonnaise | 20 | 0.03125 |
| Total | 640 | 1 |

Meanwhile, in operation (S220), a material mix ratio intake is calculated based on the food intake per person, but, in the food intake information corresponding to the food searched in the food intake database 131, in a case of two persons, a material mix ratio intake may be estimated based on the total thereof, or the average intake may be calculated and a material mix ratio intake may then be estimated. In a case in which the material mix ratio intake is estimated based on the total thereof, estimation of the food commodity intake is preferably carried out by dividing the total by the person number to obtain an average food commodity intake. Food intakes may be obtained by various other methods.

Next, the food commodity detection portion 125 detects whether the material contained in the material mix ratio intake is a food commodity (S225). In operation (S225), the materials that are regarded as being food commodities are the same as in Table 3 and the materials that are regarded as being not food commodities are the same as in Table 4.

TABLE 3

Hamburger raw material mix ratio

| Material | Unit (g) | Ratio |
|---|---|---|
| Mushroom | 50 | 0.0078125 |
| Lettuce | 100 | 0.15625 |
| Tomato | 100 | 0.15625 |
| Onion | 50 | 0.078125 |
| Beef | 50 | 0.078125 |
| Pork | 60 | 0.09375 |

TABLE 4

Hamburger raw material mix ratio

| Material | Unit (g) | Ratio |
|---|---|---|
| Hamburger bread | 60 | 0.09375 |
| Pickles | 100 | 0.15625 |
| Ketchup | 20 | 0.03125 |
| Mayonnaise | 20 | 0.03125 |
| Cheese (slice) | 30 | 0.046875 |

Next, the food commodity database accumulation portion 127 accumulates weight data of material that is regarded as food commodity, as shown in Table 5 (S230).

TABLE 5

Raw material food accumulation data (before sum)

| Material | Unit (g) | Ratio |
|---|---|---|
| Strong flour | 32.96706 | 0.051511 |
| Egg | 18.18182 | 0.028409 |
| Pork | 60 | 0.09375 |
| Garlic | 0.5848 | 0.000914 |
| Water | 21.09888 | 0.032967 |
| Water | 37.3134 | 0.058302 |
| Water | 1.7896486 | 0.002807 |
| Water | 13.4328 | 0.020989 |
| Water | 1.163635 | 0.001818 |
| Sugar | 1.63742 | 0.002558 |
| Sugar | 13.9925 | 0.021863 |
| Salt | 0.5 | 0.000781 |
| Salt | 0.65934 | 0.00103 |
| Salt | 1.1194 | 0.001749 |
| Salt | 0.70176 | 0.001097 |
| Beef | 50 | 0.078125 |
| Shortening | 2.14284 | 0.003348 |
| Cooking oil | 0.60606 | 0.000947 |
| Acetic acid | 0.074854 | 0.000117 |
| Acetic acid | 0.5597 | 0.000875 |
| Acetic acid | 0.048485 | 7.58E−05 |
| Lettuce | 100 | 0.15625 |
| Mushroom | 50 | 0.078125 |
| Anion | 1.1696 | 0.001828 |
| Anion | 50 | 0.078125 |
| Cucumber | 33.5821 | 0.052472 |
| Milk | 29.5 | 0.046094 |
| Yeast | 0.98904 | 0.001545 |
| Powdered skim milk | 0.85716 | 0.001339 |
| Tomato | 100 | 0.15625 |
| Tomato | 14.03508 | 0.02193 |
| Brown sugar | 1.28574 | 0.002009 |
| Total | 640 | 1 |

Next, the food commodity detection portion 125 determines whether all materials contained in the material mix ratio intake are food commodities (S235).

When a material that is not a food commodity is contained in the material mix ratio intake (S235—N), operations (S215) to (S230) are repeated until the material that is not a food commodity is not contained therein.

Meanwhile, when all materials are food commodities (S235—Y), the food commodity intake conversion portion 129 sums all weight data finally accumulated as shown in Table 5, for each food commodity, as shown in Table 6 (S240) to obtain a food commodity intake and updates the food commodity intake on the food commodity intake database 143 (S245).

TABLE 6

Raw material food (after summation)

| Material | Unit (g) | Ratio |
| --- | --- | --- |
| Strong flour | 32.96706 | 0.051511 |
| Egg | 18.18182 | 0.028409 |
| Pork | 60 | 0.09375 |
| Garlic | 0.5848 | 0.000914 |
| Water | 74.8052 | 0.116883 |
| Sugar | 15.62992 | 0.024422 |
| Salt | 2.9805 | 0.004657 |
| Beef | 50 | 0.078125 |
| Shortening | 2.14284 | 0.003348 |
| Cooking oil | 0.60606 | 0.000947 |
| Acetic acid | 0.683039 | 0.001067 |
| Lettuce | 100 | 0.15625 |
| Mushroom | 50 | 0.078125 |
| Onion | 51.1696 | 0.079953 |
| Cucumber | 33.5821 | 0.052472 |
| Milk | 29.5 | 0.046094 |
| Yeast | 0.98904 | 0.001545 |
| Powdered skim milk | 0.85716 | 0.001339 |
| Tomato | 114.0351 | 0.17818 |
| Brown sugar | 1.28574 | 0.002009 |
| Total | 640 | 1 |

Meanwhile, when, in operations (S205) to (S245) according to the present invention, a material not contained in the food intake database 131 or food commodity mix ratio database 133 is present, the material is added to the unregistered commodity database 141 to construct an unregistered commodity database.

The present invention provides a computer-readable storage medium storing program instruction, which performs the various processes of the above-described embodiments of the present invention and which can be executed by a variety of computers. The computer-readable storage medium records programs to execute the aforementioned method for estimating food commodity intakes. The computer-readable storage medium may include program instructions, data files and data structures or a combination thereof. Examples of the computer-readable storage medium may include a magnetic medium such as a hard disk, floppy disc or magnetic tape, an optical recording medium such as compact disc-read only memory (CD-ROM) or digital versatile disc (DVD), a magneto-optical medium such as a floptical disc, and a hardware device particularly established to store and execute program instructions, such as a ROM, random access memory (RAM) or flash memory. The computer-readable storage medium may be a transmission medium including a carrier for transmitting signals indicating program instructions and data structures, such as an optical fiber, a metal wire or a wave guide. Examples of a program instruction may be written not only in machine code through a compiler but also in high-level code capable of being executed by a computer using an interpreter.

According to the present invention, more accurate food intake data can be conveniently estimated by converting all ingredients of mixed foods into food commodities. When reliable food intake database can be secured through this program, various safety management operations such as estimation of exposed amount of residual pesticides in foods, determination of residue standards, and evaluation of harmfulness can be performed. Ultimately, the present invention can contribute to national safe dietary life and health enhancement. In addition, the present invention provides the basis for modifying the law and regulations so as to contribute to domestic food safety to keep pace with international food standards during import and export of agricultural products, and imparts reliability and high qualities to domestic agricultural, marine and livestock products through pesticide management databases made using food commodity intake databases, thus contributing to international trades.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A method for estimating a food commodity intake comprising:
    (a) obtaining a food intake of a food searched as a subject to be estimated for food commodity intake based on food intake database;
    (b) obtaining a material mix ratio of the food searched based on the material mix ratio database and estimating a material mix ratio intake using the food intake;
    (c) detecting whether or not the material contained in the material mix ratio intake estimation results is a food commodity;
    (d) accumulating a weight data of the material that is detected to be a food commodity among the materials obtained from the material mix ratio intake estimation results;
    (e) repeatedly performing operations (b) to (d) on materials that are not food commodities, until all of the materials contained in the material mix ratio intake estimation results become food commodities; and
    (f) summing the accumulated weight data of each food commodity to estimate a food commodity intake of the food, when all of the materials contained in the material mix ratio intake estimation results are food commodities.

2. The method according to claim 1, further comprising:
    updating the estimated food commodity intake on food commodity intake databases.

3. The method according to claim 1, further comprising:
    adding a material contained in the intake database, among materials contained in the food the material mix ratio intake estimation results, to an unregistered commodity database, wherein the unregistered commodity database is established with information on materials not registered in the food intake database.

4. The method according to claim 1, wherein the food intake database is established from the results obtained from the Korea National Health And Nutrition Examination Survey (KNHANES).

5. A computer-readable storage medium storing a program to execute the method according to claim 1.

6. A system for estimating a food commodity intake comprising:
    a material mix ratio intake conversion portion to estimate a material mix ratio intake of a material mix ratio of a food searched using a food intake and a material mix ratio database of the food searched as a subject to be estimated for a food commodity intake based on the food intake database;

a food commodity detection portion to detect whether or not the material contained in the material mix ratio intake estimation results is a food commodity;

a food commodity data accumulation portion to accumulate a weight data of the material that is detected to be a food commodity contained in the material mix ratio intake estimation results; and a food commodity intake conversion portion to calculate a total of the accumulated weight data of each food commodity to estimate a food commodity intake of the food, when all of the materials contained in the material mix ratio intake estimation results are food commodities, wherein the system repeats conversion of material mix ratio intake, detection of food commodity and accumulation of material weight data on the materials that are not food commodities, until all of the materials contained in the material mix ratio intake become food commodities.

7. The system according to claim 6, wherein the food commodity intake conversion portion updates the estimated food commodity intake on the food commodity intake database.

8. The system according to claim 6, wherein the food intake database is established from the results obtained from the Korea National Health And Nutrition Examination Survey (KNHANES).

* * * * *